US009446183B2

(12) United States Patent
Smith et al.

(10) Patent No.: US 9,446,183 B2
(45) Date of Patent: *Sep. 20, 2016

(54) PUMPING SYSTEM AND METHOD FOR ASSISTING A PATIENT'S HEART

(71) Applicant: Cardiac Assist, Inc., Pittsburgh, PA (US)

(72) Inventors: Douglas E. Smith, Jefferson, NC (US); Jennifer Wivholm, Pittsburgh, PA (US); Robert G. Svitek, Freeport, PA (US); Cory J. Cortese, Pittsburgh, PA (US); Robert Bollinger, Pittsburgh, PA (US); Michael Garippa, Pittsburgh, PA (US)

(73) Assignee: CardiacAssist, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/810,701

(22) Filed: Jul. 28, 2015

(65) Prior Publication Data

US 2015/0328390 A1 Nov. 19, 2015

Related U.S. Application Data

(63) Continuation of application No. 14/615,496, filed on Feb. 6, 2015, now Pat. No. 9,168,334, which is a continuation of application No. 14/035,087, filed on Sep. 24, 2013, now Pat. No. 8,979,742, which is a continuation of application No. 12/655,491, filed on Dec. 31, 2009, now Pat. No. 8,562,519.

(51) Int. Cl.
*A61M 1/00* (2006.01)
*A61M 1/36* (2006.01)

(Continued)

(52) U.S. Cl.
CPC ......... *A61M 1/3659* (2014.02); *A61M 1/1006* (2014.02); *A61M 1/1698* (2013.01); *A61M 1/3621* (2013.01); *A61M 1/3653* (2013.01);

(Continued)

(58) Field of Classification Search
CPC .......................... A61B 1/0638; A61M 1/3659
USPC ....................... 600/16, 160, 17, 18
See application file for complete search history.

(56) References Cited

U.S. PATENT DOCUMENTS 3,152,340 A 10/1964 Fry et al.
3,884,808 A 5/1975 Scott (Continued)

OTHER PUBLICATIONS

Yano et al. "The Feasibility and Efficacy of Right Ventricular Assistance without Thoracotomy" ASAIO Journal. 1993. pp. 120-125.

(Continued)

*Primary Examiner* — Theodore Stigell
*Assistant Examiner* — Nadia A Mahmood
(74) *Attorney, Agent, or Firm* — The Webb Law Firm

(57) ABSTRACT

A cannula for a patient includes an elongate body having a length of at least 70 cm and a channel extending through the body defining a wall. The cannula includes a wire embodied within at least a portion of the wall. The body has a proximal end, a distal end having a tip opening through which the channel extends and a plurality of side holes through the wall in proximity to the tip for unimpeded flow of blood at the distal end. The cannula includes a barbed fitting at the proximal end. The cannula includes a suture wing for securing the elongated body to the patient. A system for assisting a patient's heart. A method for assisting a patient's heart.

27 Claims, 5 Drawing Sheets

(51) Int. Cl.
*A61M 1/10* (2006.01)
*A61M 25/01* (2006.01)
*A61M 1/16* (2006.01)
*A61M 25/00* (2006.01)

(52) U.S. Cl.
CPC ......... *A61M 1/3666* (2013.01); *A61M 25/007* (2013.01); *A61M 25/0041* (2013.01); *A61M 25/0108* (2013.01); *A61M 25/005* (2013.01); *A61M 2025/0004* (2013.01); *A61M 2025/0008* (2013.01); *A61M 2205/32* (2013.01); *A61M 2210/125* (2013.01)

(56) References Cited

U.S. PATENT DOCUMENTS

| | | |
|---|---|---|
| 4,573,997 A | 3/1986 | Wisman et al. |
| 4,871,358 A | 10/1989 | Gold |
| 4,927,407 A | 5/1990 | Dorman |
| 4,994,027 A | 2/1991 | Farrell |
| 5,044,897 A | 9/1991 | Dorman |
| 5,079,467 A | 1/1992 | Dorman |
| 5,171,218 A | 12/1992 | Fonger et al. |
| 5,190,528 A | 3/1993 | Fonger et al. |
| 5,308,319 A | 5/1994 | Ide et al. |
| 5,314,418 A | 5/1994 | Takano et al. |
| 5,330,433 A | 7/1994 | Fonger et al. |
| 5,376,114 A | 12/1994 | Jarvik |
| 5,449,342 A | 9/1995 | Hirose et al. |
| 5,599,306 A | 2/1997 | Klein et al. |
| 5,711,753 A | 1/1998 | Pacella et al. |
| 5,810,758 A | 9/1998 | Yamazaki et al. |
| 5,840,070 A | 11/1998 | Wampler |
| 5,885,238 A | 3/1999 | Stevens et al. |
| 5,916,193 A | 6/1999 | Stevens et al. |
| 5,928,181 A | 7/1999 | Coleman et al. |
| 5,931,829 A | 8/1999 | Burbank et al. |
| 5,954,696 A | 9/1999 | Ryan |
| 5,957,879 A | 9/1999 | Roberts et al. |
| 6,045,496 A | 4/2000 | Pacella et al. |
| 6,083,260 A | 7/2000 | Aboul-Hosn |
| 6,090,096 A | 7/2000 | St. Goar et al. |
| 6,110,139 A | 8/2000 | Loubser |
| 6,135,943 A | 10/2000 | Yu et al. |
| 6,162,167 A | 12/2000 | Goldstein et al. |
| 6,217,546 B1 | 4/2001 | Hinchliffe et al. |
| 6,443,884 B1 | 9/2002 | Miyawaki |
| 6,447,441 B1 | 9/2002 | Yu et al. |
| 6,497,698 B1 | 12/2002 | Fonger et al. |
| 6,676,650 B1 | 1/2004 | Magovern et al. |
| 6,685,621 B2 | 2/2004 | Bolling et al. |
| 6,716,189 B1 | 4/2004 | Jarvik et al. |
| 6,790,171 B1 | 9/2004 | Grundeman et al. |
| 6,808,482 B1 | 10/2004 | Pacella et al. |
| 6,808,508 B1 | 10/2004 | Zafirelis et al. |
| 7,022,100 B1 | 4/2006 | Aboul-Hosn et al. |
| 7,267,660 B2 | 9/2007 | Fonger et al. |
| 2003/0208097 A1 | 11/2003 | Aboul-Hosn et al. |
| 2004/0034272 A1 | 2/2004 | Diaz et al. |
| 2005/0004421 A1 | 1/2005 | Pacella et al. |
| 2005/0085772 A1 | 4/2005 | Zafirelis et al. |
| 2007/0161845 A1 | 7/2007 | Magovern et al. |

OTHER PUBLICATIONS

Matsuo et al. "Potentialities and Problems of a Novel Bilateral Ventricular Assist System Without Thoracotomy" Artificial Organs. 2000. pp. 148-155. 24(2). International Society for Artificial Organs.

Yano et al. "Efficacy and Safety of a Percutaneous Right Ventricular Assist System" Annals of Thoracic Surgery. 1996. pp. 1231-1235. vol. 61. The Society of Thoracic Surgeons.

Frazier et al. "First Clinical Use of the Redesigned HeartMate II Left Ventricular Assist System in the United States" Texas Heart Institute Journal. 2004. pp. 157-159. 31(2). Texas Heart Institute.

Toporoff et al. "Pulmonary Complications of a Roller Pump Right Ventricular Assist Device" Journal of Surgical Research. 1988. pp. 21-27. vol. 45.

Rose et al. "Technique and Results with a Roller Pump Left and Right Heart Assist Device" Annals of Thoracic Surgery. 1989. pp. 124-129. vol. 47. The Society of Thoracic Surgeons.

Babic et al. "Non-Surgical Left-Atrial Aortic Bypass" The Lancet. Dec. 17, 1988. pp. 1430-1431.

Pavie et al. "Left Centrifugal Pump Cardiac Assist with Transseptal Percutaneous Left Atrial Cannula" Artificial Organs. 1998. pp. 502-507. 22(6). International Society for Artificial Organs.

Hall et al. "An Experimental Study of Prolonged Left Heart Bypass Without Thoracotomy" Annals of Surgery. Aug. 1962. pp. 190-196. 156(2).

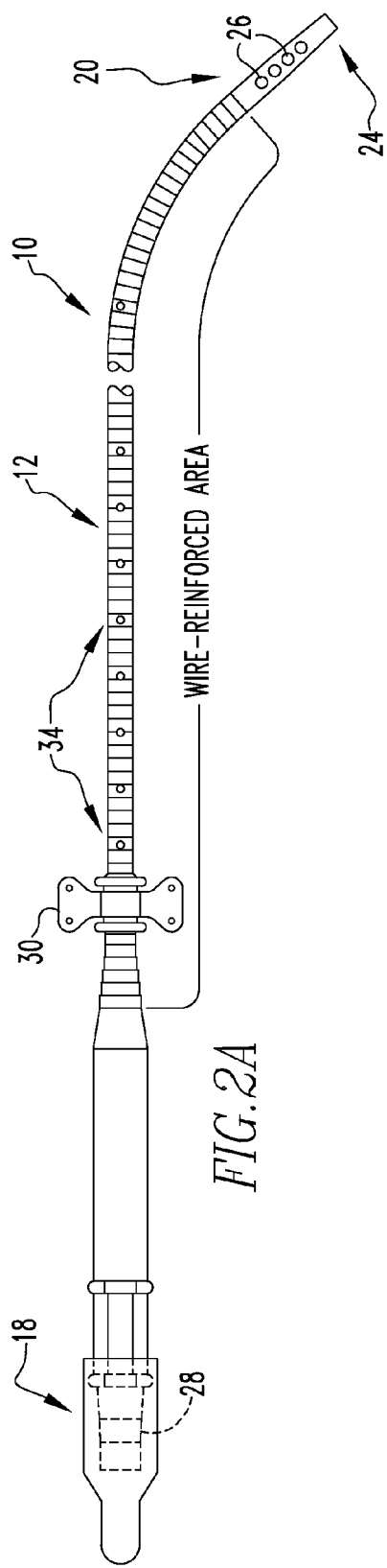
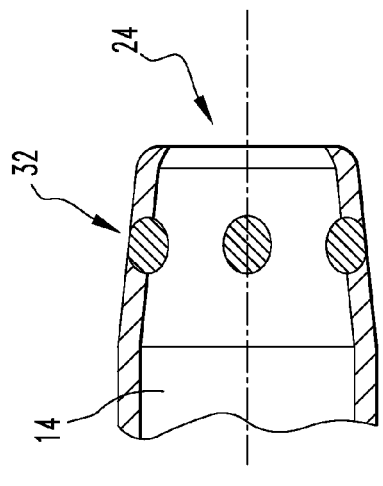
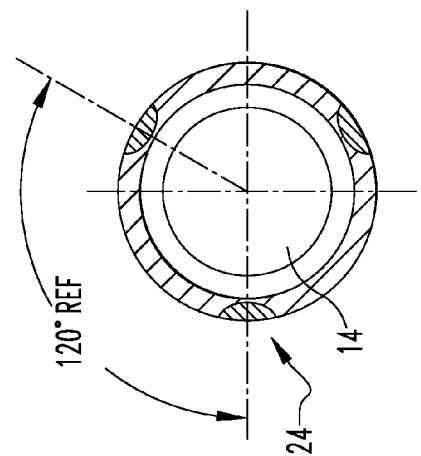
FIG.2A
FIG.2B
FIG.2C

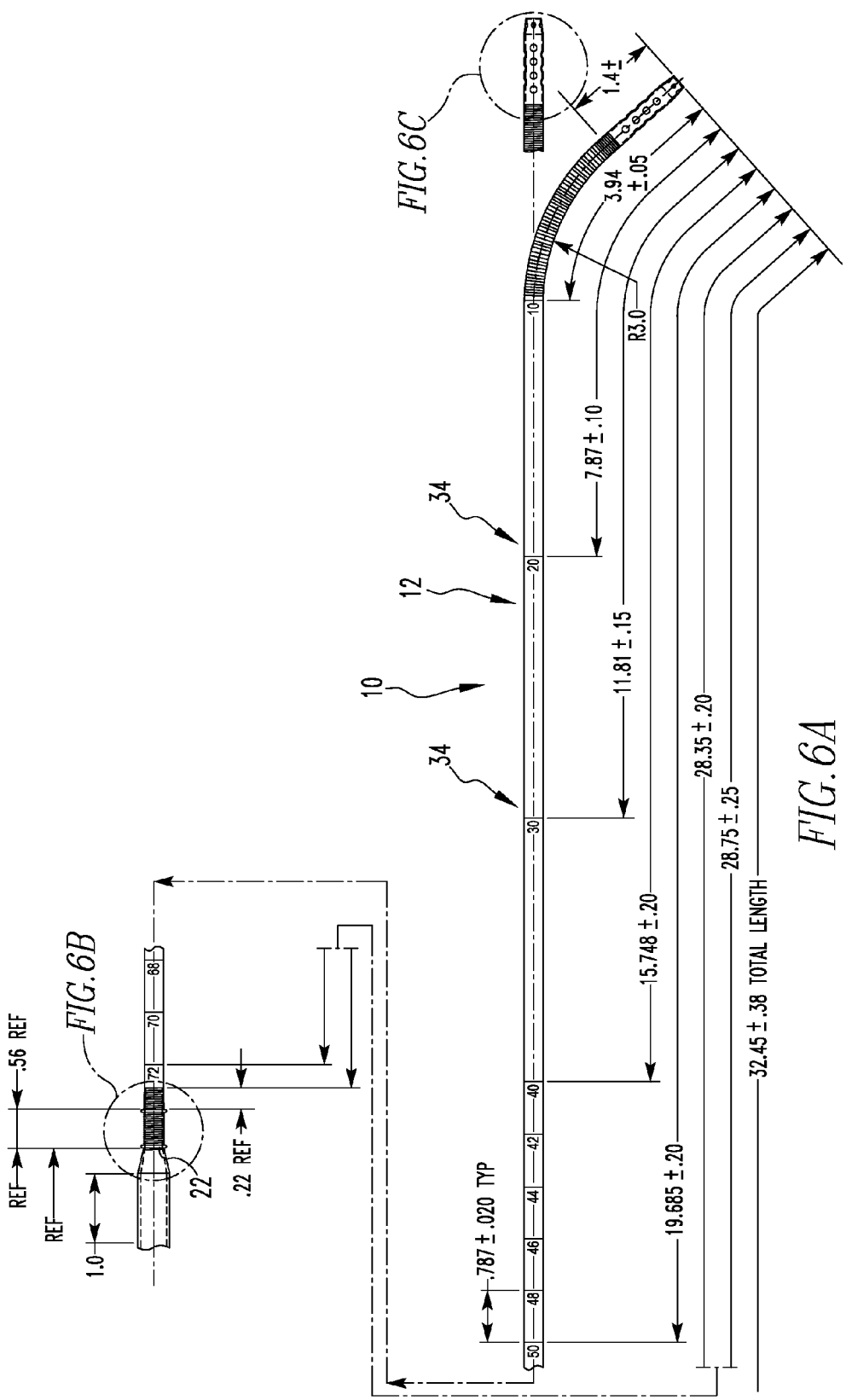

PUMPING SYSTEM AND METHOD FOR ASSISTING A PATIENT'S HEART

This application is a continuation of U.S. patent application Ser. No. 14/615,496 filed Feb. 6, 2015 and entitled "Pumping System and Method for Assisting a Patient's Heart", which is published as United States Publication No. 2015/0165111 A1 and which is a continuation of U.S. patent application Ser. No. 14/035,087, filed Sep. 24, 2013 and entitled "Pumping System and Method for Assisting a Patient's Heart", now U.S. Pat. No. 8,979,742, which is a continuation of U.S. patent application Ser. No. 12/655,491, filed Dec. 31, 2009 and entitled "Pumping System and Method for Assisting a Patient's Heart", now U.S. Pat. No. 8,562,519 to Smith et al.

FIELD OF THE INVENTION

The present invention is related to assisting a patient's heart with a cannula. (As used herein, references to the "present invention" or "invention" relate to exemplary embodiments and not necessarily to every embodiment encompassed by the appended claims.) More specifically, the present invention is related to assisting a patient's heart with a cannula where the cannula is of a length that extends from the patient's groin to the pulmonary artery.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Patients with severe Right-sided circulatory/Right Ventricular Failure have a significantly high mortality and morbidity caused by a multitude of factors in multiple patient populations. Historically, Right Ventricular Assist Devices have been placed for surgical patients, without a percutaneous or Cath lab option available. These surgical RVAD's have been placed for patients with right inferior myocardial infarction, acute right-sided ischemic myocardial, infarctions (with large left and right propagation), Cardiogenic Shock, LVAD created RV dysfunction, post transplant RV failure and pulmonary hypertension. Acute myocardial infarction and Cardiogenic shock have been treated with IABPs and maximal inotropic support, to which many patients become refractory to these treatment options. Surgically implanted LVADs can create a significant septal shift that leads to a dynamic change in the Starling curve that abruptly places patients into severe RV Failure. Patients bridged to transplant to from an LVAD with severe RV failure, can limit post transplant survival. Secondary Pulmonary Hypertension leads to an exacerbation of RV failure in acute and chronic situations, which are commonly treated with LVADs.

The present invention, often referred to as a TandemHeart Transseptal Cannula EF 72, ("THTC-EF-72") has the capabilities to reach the Pulmonary Artery from the Femoral Veins via a percutaneous insertion. Traditional RVADs have a cannula either primarily placed in the PA or a graft sewn onto the PA, then a cannula inserted through the graft. The THTC-EF 72 can be quickly visualized in the PA via Fluoroscopy and X-Ray with the aid of the distal markers in the cannula, verifying the proper orientation of the outflow to the patient.

The THTC-EF 72 facilitates greater usage of the TandemHeart System in a wider population of patients requiring Left-sided extracorporeal circulatory support. Torso length can limit the ability to access the Left Atrium via percutaneous insertion. The THTC-EF 72 can be utilized by either the Left or Right Femoral Vein, optimizing placement. Venous and Arterial blood mixing in patients can lead to an increase of morbidity and mortality.

Furthermore, traditional venoarterial ECMO (VA ECMO) is the current standard of care used to treat right ventricular failure and respiratory failure percutaneously. VA ECMO takes blood from the right atrium and pumps it through an oxygenator and back into the arterial circulation via the femoral artery. VA ECMO bypasses the lungs and the heart completely. Therefore, residual blood is left stagnant in both the heart and lungs potentially leading to thrombosis and an inadequately unloaded right ventricle. Additionally, the arterial cannulation can lead to problems including but not limited to bleeding, stroke, and infection.

Often, a patient has a problem with the right femoral vein (potentially thrombosis) that prevents transseptal cannulation from the right leg. A 62 cm cannula of the prior art cannot be used to access the left atrium from the left femoral vein because it is often too short. This problem was not recognized until after commercialization. The cannula of the present invention solves that problem.

BRIEF SUMMARY OF THE INVENTION

The present invention pertains to a cannula for a patient. The cannula comprises an elongate body having a length of at least 70 cm and a channel extending through the body defining a wall. The cannula comprises a wire embodied within at least a portion of the wall. The body has a proximal end, a distal end having a tip opening through which the channel extends and a plurality of side holes through the wall in proximity to the tip for unimpeded flow of blood at the distal end. The cannula comprises a barbed fitting at the proximal end. The cannula comprises a suture wing for securing the elongated body to the patient.

The present invention pertains to a system for assisting a patient's heart. The system comprises a pump adapted to be disposed outside the patient which pumps blood. A system comprises a drainage cannula that is adapted to extend from the right atrium of the heart in fluid communication with the pump to provide blood to the pump. The system comprises a pulmonary artery cannula adapted to extend from the patient's groin to the pulmonary artery of the patient to provide blood to the pulmonary artery. The pulmonary artery cannula is in fluid communication with the pump, whereby the heart's right ventricle is essentially bypassed by draining the right atrium and pumping blood into the pulmonary artery thereby allowing the right ventricle of the patient to rest and enable right ventricular support.

The present invention pertains to a method for assisting a patient's heart. The method comprises the steps of inserting the tip of a cannula into a right femoral vein of a patient. There is the step of moving the tip through the right femoral vein until side holes of the cannula in proximity to the tip are disposed in the pulmonary artery. There is the step of inserting a tip of a drainage cannula into the patient. There is the step of moving the tip of the drainage cannula through the patient until the tip of the drainage cannula is disposed in the right atrium. There is the step of connecting an inlet of a pump to the drainage cannula with connective tubing. There is the step of connecting an outlet of the pump to the pulmonary artery cannula with connective tubing. There is the step of connecting an outlet of the oxygenator to the cannula with connective tubing. There is the step of securing the pump to the patient. There is the step of pumping blood received by the pump from the drainage cannula into the pulmonary artery through the pulmonary artery cannula to provide right ventricular and respiratory support without having to bypass the heart and lungs.

BRIEF DESCRIPTION OF THE SEVERAL VIEWS OF THE DRAWING

In the accompanying drawings, the preferred embodiment of the invention and preferred methods of practicing the invention are illustrated in which:

FIG. 2A is a side view of the cannula of the present invention.

FIG. 2B is an axial view of the tip of the cannula of FIG. 2A.

FIG. 2C is an exploded side view of the cannula of FIG. 2A.

FIG. 6A is a side view of the cannula of the present invention.

DETAILED DESCRIPTION OF THE INVENTION

Figure 5:
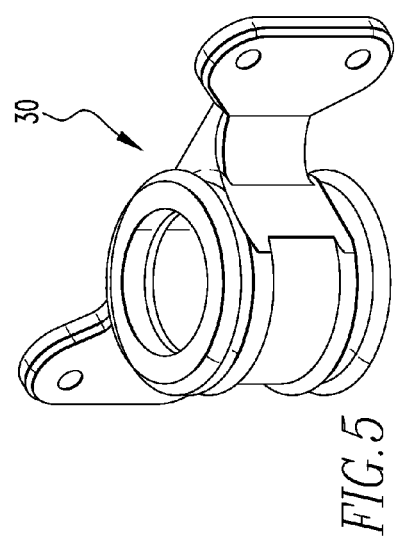
FIG. 5 is a perspective view of a suture wing.

Referring now to the drawings wherein like reference numerals refer to similar or identical parts throughout the several views, and more specifically to FIGS. 2a, 2b, 2c and 6 thereof; there is shown a cannula 10 for a patient. The cannula 10 comprises an elongate body 12 having a length of at least 70 cm and a channel 14 extending through the body 12 defining a wall 16. The cannula 10 comprises a wire 22 embodied within at least a portion of the wall 16. The body 12 has a proximal end 18, a distal end 20 having a tip 24 opening through which the channel 14 extends and a plurality of side holes 26 through the wall 16 in proximity to the tip 24 for unimpeded flow of blood at the distal end 20. The cannula 10 comprises a barbed fitting 28 at the proximal end 18. The cannula 10 comprises a suture wing 30, as shown in FIG. 5, for securing the elongated body 12 to the patient. The pump 38 can be any centrifugal, axial, mixed, or roller pump that can produce adequate flowrates through the system. Several examples include but are not limited to the TandemHeart, Medtronic Biomedicus (BP-50, BP-80, BP-80.times.), Jostra Rotaflow, Levitronix Centrimag, Terumo Capiox, Sarns Delphin, Cobe Revolution, and others. The pump 38 can be secured to the patient for instance with a holster 52 that holds the pump with a strap or in a pocket. The holster 52 can be wrapped around the leg of the patient.

The distal end 20 may be curved for natural anatomical placement from the inferior vena cava into the left atrium of. At least a portion of the elongate body 12 may have insertion depth markings 34. The tip 24 may have radiopaque markers 32 to aid in visualization.

Figure 1:
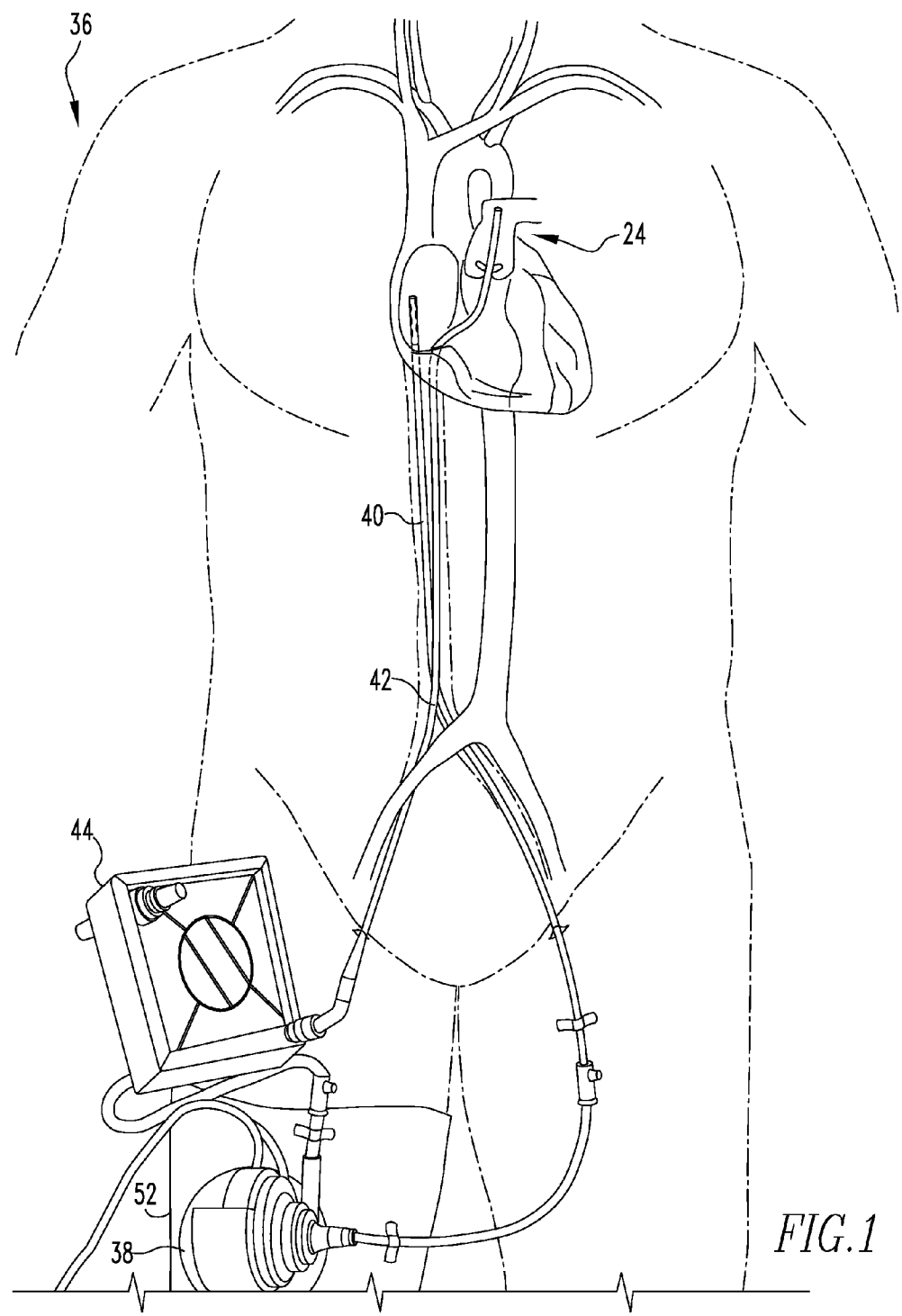
FIG. 1 is a schematic representation of the system of the present invention.

The present invention pertains to a system 36 for assisting a patient's heart, as shown in FIG. 1. The system 36 comprises a pump 38 adapted to be disposed outside the patient's which pumps blood. A system 36 comprises a drainage cannula 40 that is adapted to extend from the right atrium of the heart in fluid communication with the pump 38 to provide blood to the pump 38. The system 36 comprises a pulmonary artery cannula 42 that is at least 70 cm in length and adapted to extend from the patient's groin to the pulmonary artery of the patient to provide blood to the pulmonary artery. The pulmonary artery cannula 42 is in fluid communication with the pump 38, whereby the heart's right ventricle is essentially bypassed by draining the right atrium and pumping blood into the pulmonary artery thereby allowing the right ventricle of the patient to rest and enable right ventricular support.

The system 36 may include an oxygenator 44 in fluid communication with the pump 38 which receives blood pumped by the pump 38 and oxygenates the blood, and with the pulmonary artery cannula 42 to provide blood oxygenated by the oxygenator 44 to the pulmonary artery. The oxygenator 44 can be any of the spiral wound sheet membrane type or any of the hollow fiber membrane type including but not limited to the Terumo Capiox, Medtronic Minimax, Medtronic ECMO Oxygenators, Medtronic Affinity, Jostra Quadrox, Gish Vision, Cobe Optima, and others. A controller that may be used for the pump is described in U.S. Pat. No. 6,808,508 or in U.S. patent application Ser. No. 11/328,961; now U.S. Pat. No. 8,550,973 to Magovern et al., both of which are incorporated by reference herein.

The present invention pertains to a method for assisting a patient's heart. The method comprises the steps of inserting the tip 24 of a cannula 10 having a length of at least 70 cm into a right femoral vein of a patient. There is the step of moving the tip 24 through the right femoral vein until side holes 26 of the cannula 10 in proximity to the tip 24 are disposed in the pulmonary artery. There is the step of inserting a tip 24 of a drainage cannula 40 into the patient. There is the step of moving the tip 24 of the drainage cannula 40 through the patient until the tip 24 of the drainage cannula 40 is disposed in the right atrium. There is the step of connecting an inlet of a pump 38 to the drainage cannula 40 with connective tubing. There is the step of connecting an outlet of the pump 38 to the pulmonary artery cannula 42 with connective tubing. There is the step of connecting an outlet of the oxygenator 44 to the cannula 10 with connective tubing. There is the step of securing the pump 38 to the patient. There is the step of pumping blood received by the pump 38 from the drainage cannula 40 into the pulmonary artery through the pulmonary artery cannula 42 to provide right ventricular and respiratory support without having to bypass the heart and lungs.

There may be the steps of connecting the outlet of the pump 38 to an inlet of an oxygenator 44 with connective tubing; connecting an outlet of the oxygenator 44 to the pulmonary artery cannula 42 with connective tubing; and the pumping step may include the step of pumping blood received by the pump 38 from the drainage cannula 40 through the oxygenator 44, where oxygen is provided to the blood and carbon dioxide is removed from the blood, and into the pulmonary artery through the pulmonary artery cannula 42. The step of inserting the tip 24 of the drainage cannula 40 may include the step of inserting the tip 24 of the drainage cannula 40 into the left femoral vein.

Figure 3:
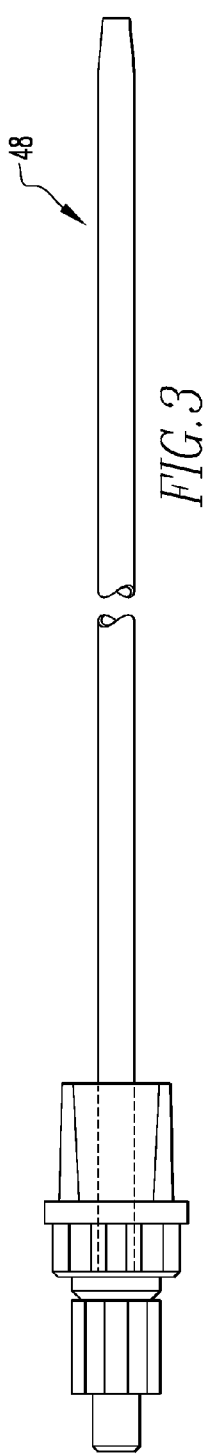
FIG. 3 is a side view of an introducer.
Figure 4:
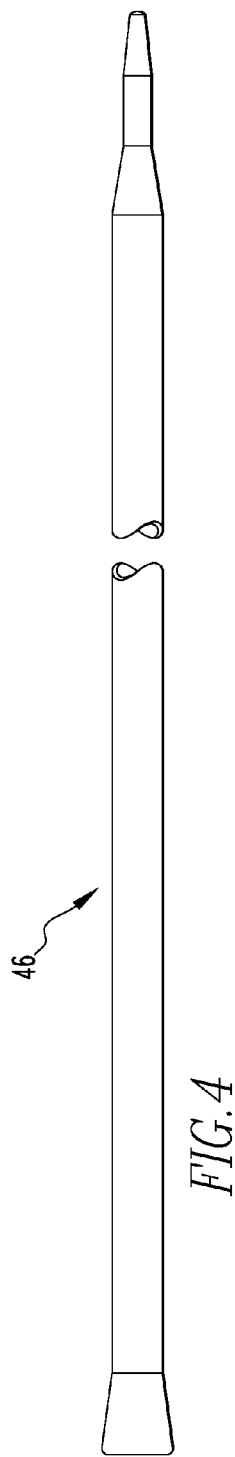
FIG. 4 is a side view of a dilator.

In the operation of the invention, the THTC-EF 72 Set consists of three components: a 21 Fr cannula, an introducer 48 (see FIG. 3), and a 14/21 Fr Two-Stage dilator 46 (see FIG. 4).

Figure 6B:
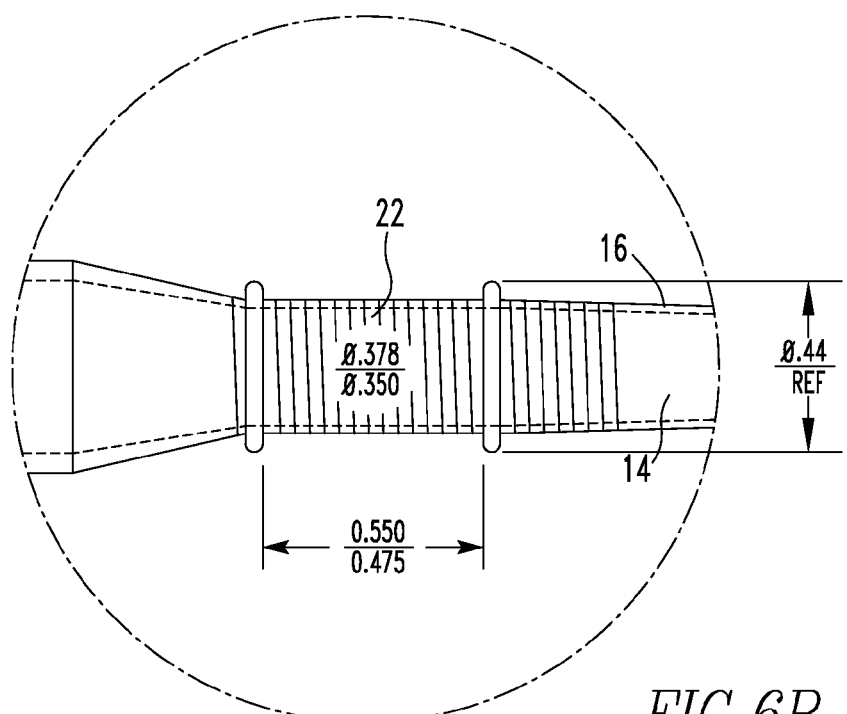
FIG. 6B is a detail view of detail 6B in FIG. 6A.
Figure 6C:
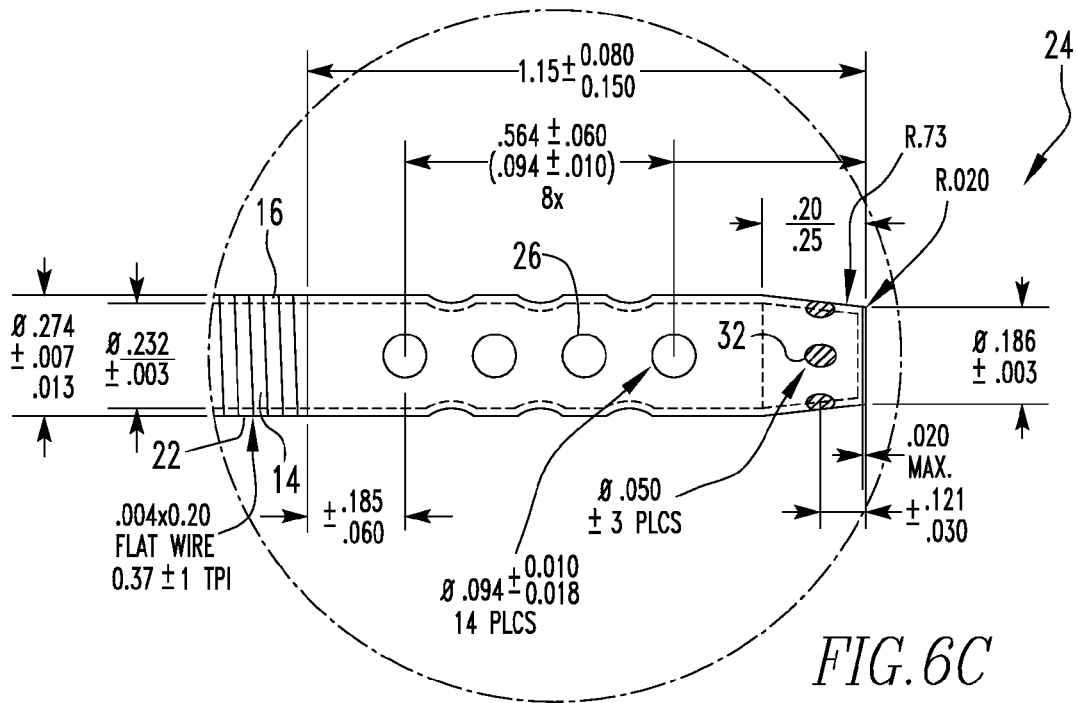
FIG. 6C is a detail view of detail 6C in FIG. 6A.

The THTC-EF 72 cannula (FIG. 6) has a 21 Fr dipped polyurethane body 12 with a spring-like coil of wire 22 embedded into the cannula 10 wall 16. The cannula 10 has a working length of about 72 cm. The wire-reinforced area allows for clear visualization under fluoroscopy and for resistance to kinking. The wire-reinforcing also permits a thin-walled construction. This feature allows for a larger inside diameter (lumen) while maintaining the 21 Fr outside diameter. Printing on a region of the cannula 10 which is not wire-reinforced indicates the area where a clamp should be applied as needed during the set-up or removal process. The distal end 20 of the cannula 10 is curved for natural anatomical placement from the inferior vena cava into the left atrium. The cannula 10 tip 24 has 14 side holes 26 in addition to the tip 24 opening for unimpeded inflow of blood at the distal end 20, a barbed fitting 28 at the proximal end 18, and insertion depth markings 32 from 40 to 72 cm measured from the distal end 20. The tip 24 of the THTC-EF 72 cannula 10 contains radiopaque markers 32 which are embedded in the cannula 10 to aid in visualization. The cannula 10 also includes a Suture Wing 30 to provide a means for securing the cannula 10 to the patient. The printing on the cannula 10 is oriented to show the clinician that the distal tip 24 curves to the right when the printing is on the top of the cannula 10 body 12. FIG. 6 shows a 21 Fr Wire-Reinforced THTC-EF 72 cannula.

The Introducer 48 is a tube that fits inside the THTC-EF 72 (FIG. 3) during insertion into the patient's vasculature. The Introducer 48 consists of a tube which is insert-molded to a male Luer hub. A hemostasis cap is used on the THTC-EF 72 Introducer 48 to cover the proximal end 18 of the THTC-EF 72 cannula 10 to prevent blood loss. Small holes in the side of the introducer 48 at both the proximal and distal ends facilitate aspiration. The introducer 48 has a 14 Fr outside diameter.

The purpose of the Introducer 48 is to guide the cannula 10/introducer 48 assembly over a guidewire, across the septum, into the left atrium, and to provide a lumen for the injection of contrast media to help guide the placement of the cannula 10. Contrast media is emitted from the proximal tip of the introducer 48. FIG. 3 shows a THTC-EF 72 Introducer 48.

The dilator 46 (FIG. 4) is a slightly stiffer, stepped 2-diameter tube which is inserted prior the cannula 10/introducer 48 assembly. The inner lumen of the dilator 46 allows the dilator 46 to be inserted into the patient over a guidewire previously placed into the left atrium. The proximal end 18 of the THTC-EF 72 dilator 46 is formed to aid in gripping. The Dilator 46 serves to dilate the hole in the fossa ovalis and facilitate access to the left atrium. It is withdrawn and discarded after use. FIG. 4 shows a 14/21 Fr. dilator 46. The cannula 10 is the only component of the cannula/dilator/oburator set left in place during therapy. Its purpose is to provide the conduit for blood flow from the pump 38.

Mechanical Characteristics:

| Shape | Single lumen tube, curved tip | Straight, single lumen tube | 2 stage stepped tapered single lumen tube |
|---|---|---|---|
| Radiopaque | Yes | Yes | Yes |
| Overall length | 34.25 in. (87 cm) | 36.25 in. (92.1 cm) | 32.65 in. (82.9 cm) |
| Working length | 28.4 in. (72 cm) | 35.35 in. (89.8 cm) | 32.65 in. (82.9 cm) |
| Outer diameter | 21 Fr | 14 Fr. | 14/21 Fr. |
| Inner diameter | 0.232 in. (.59 cm) | 0.111 in. (0.28 cm) | 0.175 in. (0.44 cm) |
| Distal tip | Tapered with an end opening of 0.186 in. (.47 cm) and 7 pairs (14 total) of side holes 0.094 in. (2.4 mm) diameter | Tapered with 0.041 in. ± 0.002 in. (1.0 mm) opening at tip | Tapered 14 Fr. to 21 Fr. with 0.040 in. ± 0.003 in. (0.9 mm) diameter opening at tip |
| Connectors | 3/8 in. barbed connector, Polycarbonate | Luer, ABS | None |
| Materials | 42D Polyurethane, Isoplast, medical-grade stainless steel wire, Tantalum Dot | Tecoflex polyurethane, Polyethylene, ABS. radiopacifier (barium sulfate) | Polyethylene (Equistar Petrothene), radiopacifer (bismuth subcarbonate) |

Manufacture

The cannula 10 is manufactured using a urethane dipping process on a steel mandrel to create the body 12 of the device. This allows for one-piece construction of the cannula 10 body 12, and provides a thin-wall with maximal flexibility. The bare mandrel is dipped into the polyurethane, and a flat wire spring is then applied over the dipped mandrel. Subsequently dipping into polyurethane completely encapsulates the wire spring.

A one inch portion of the distal tip 24 of the cannula 10 is left free of wire reinforcement to allow for side holes 26 to be punched near the cannula 10 tip 24. As the lack of wire-reinforcement makes the cannula 10 tip 24 invisible under fluoroscopy, three tantalum markers 32 are added to distal portion of the cannula 10 tip 24. Following the addition of the markers 32, the cannula 10 tip 24 receives additional dips in an increased durometer polyurethane, to provide structural integrity for this region. A 50.degree. bend is then set into the cannula 10 approximately 3 inches from the distal tip 24 of the cannula 10. Following the bending operation, depth markings 34 are printed on the outside of the cannula 10.

A portion of the proximal end 18 of the cannula 10 is also left without wire-reinforcement to allow for clamping. A 3/8".times.3/8" barbed connector is inserted into the proximal end 18 of the cannula 10 to allow for connection to extracorporeal equipment. The Introducer 48 is an extruded tube which is insert molded into a male luer hub. The Dilator 46 is also formed from an extruded tube, and tipped to provide a region that steps from 14 Fr to 21 Fr.

Right Heart Assist

Pulmonary Artery Cannula 42 (the Invention) Insertion Procedure

The invention involves a cannula 10 inserted into the pulmonary artery (PA) for right heart support. The cannula 10 delivers flow back to the patient from the pump 38. The first step is to use a percutaneous Entry Needle to access the Right Femoral Vein (RFV). A guidewire is then inserted through needle until the tip of the guide-wire sits in the upper portion of the inferior vena cava/right atrium (IVC/RA) junction. The needle can then be removed and a pulmonary wedge catheter inserted over the guidewire into the PA. The guidewire tip 24 is then threaded into the PA, and the wedge catheter is removed. The right femoral vein is then serially dilated and the proposed invention is threaded along the guidewire into the right femoral vein. The introducer can be removed when the cannula 10 is in the right ventricle. The cannula 10 can then be threaded over the wire 22 up into the PA. The curve in the cannula 10 is a feature that helps it make the turn from the right ventricle into the PA. Once the cannula's position is acceptable, the introducer/guidewire assembly is removed and the cannula 10 is clamped. The TandemHeart transseptal cannula 10 is secured to the patient's leg using suture or the suture wing 30 or suture ring feature. Another feature of the cannula 10 is the skin markings 34 that can be used to help track cannula 10 placement and ensure no cannula 10 movement during support.

Right Atrium Cannula—Used in Conjunction with the PA Cannula Insertion Procedure The right atrium can be cannulated as the inflow to the pump 38 by first using a percutaneous entry needle to access the Left Femoral Vein (LFV). A guidewire is placed through the needle until the tip 24 sits in the RA. The needle can then be removed and the vessel can be serially dilated. The inflow cannula 10 can be inserted over the guidewire until it resides in the RA/IVC junction. Once the cannula's position is acceptable, the introducer and guidewire can be removed and the cannula 10 can be clamped. The cannula 10 can be secured to the patient's leg using suture or suture wing 30 or suture ring if available.

Connecting to the Pump 38

Pre-prime the Pump 38 by slowly filling the blood chamber of the Pump 38 with Saline, making sure to remove all air, then clamp the tubings below the saline line to insure proper wet-to-wet connections. Perform a wet-to-wet connection between the Pump 38 inlet and the Right Atrium cannula 10, up to the first cannula connector barb. Check for air bubbles, if none are present, finish pushing tubing over the cannula 10 connector. Perform another wet-to-wet connection between the Pump 38 outlet and the Pulmonary artery cannula 42, which is in the PA, up to the first cannula 10 connector barb. Check for air bubbles, if none are present, finish pushing tubing over the cannula 10 connector.

Initiate support by turning the pump 38 on at low speed (RPM). Release tubing clamps on the inlet side of the Pump 38 and check for air in the outlet side of the pump 38. If there is no air present, release the remaining tubing clamps. Adjust speed (RPM) until desired flow is achieved. Caution should be taken not to over-drive the pump 38, which could result in excessive PA pressures and overloading of the lungs.

Left Heart Assist

Transseptal Cannulation

The transseptal cannula 10 is intended for providing a means for left ventricular bypass when connected to a blood pump which returns blood to the patient via the femoral artery or other appropriate site. The cannula 10 uses a wirewound construction which prevents kinking. The cannula 10 is longer, contains insertion depth markers 34, and a means for securing the device to the patient (i.e. a suture wing 30 and suture rings). The cannula 10 also includes radiopaque markers 34 at the tip 24 for correct device placement in the left atrium. The transeptal cannula 10 provides an extended length when cannulation is necessary from the left femoral vein. It is believed that no other cannula 10 has ever been able to accomplish this.

Insertion Procedure

Use standard transseptal puncture technique to gain access into the left atrium from the femoral vein. Dilate the transseptal puncture site (fossa ovalis) with a transseptal catheter. Introduce an appropriate guidewire into the left atrium. Remove the transseptal catheter leaving the guidewire in the left atrium. Advance the two stage dilator 46 over the guidewire into the left atrium to dilate the fossa ovalis. Remove the two stage dilator 46 and assemble the Introducer to the transseptal cannula 10. Advance the introducer/cannula over the guidewire into the left atrium as follows: Load the introducer/cannula onto the guidewire and advance it until the assembly abuts the Fossa Ovalis. Under fluoroscopy or cineangiography, use the radiopaque markers 32 located in the cannula tip 24 and the end of the wire reinforced section of the cannula 10 body 12 to guide placement of cannula 10 into the left atrium. Note the location of the radiopaque markers 32 in the tip 24 of the cannula 10 and record the insertion depth using the depth markers 34 on the side of the cannula 10. Remove the guidewire and introducer and clamp the transseptal cannula 10 at the clamping zone indicated on the cannula 10 as the introducer is pulled back.

Insert the arterial cannula using standard procedures and protocols. Make a wet-to-wet connection between the transseptal cannula and the tubing that is attached to the inflow port of the pump 38. Suture the transseptal cannula securely to the patient's leg using the suture wing 30 and suture rings. The suture rings may be positioned anywhere along the insertable length of the cannula to provide additional means of securement. Make a second wet-to-wet connection between the pump 38 outflow and the arterial cannula. Ensure that no air exists in the tubing and start the pump 38 to the desired flowrate.

The 72 cm long cannula 10 can enable right ventricular and respiratory support via the groin without having to bypass the heart and lungs as in VA ECMO. The 72 cm cannula is implanted on the venous side and therefore avoids the arterial cannulation typically used in VA ECMO. The circuit consists of the 72 cm cannula, a pump 38, an oxygenator 44, a drainage cannula 40, and connective tubing. The tip of the drainage cannula 40 is placed in the right atrium. The inlet of the pump 38 is connected to the drainage cannula 40 with connective tubing. The outlet of the pump 38 is connected to the inlet of the oxygenator 44 with connective tubing. The outlet of the oxygenator 44 is connected to the 72 cm cannula whose tip 24 is placed into the pulmonary artery. The 72 cm cannula is inserted into the PA as described in the procedure referenced earlier. Oxygen or room air is used as the 'sweep gas' through the oxygenator 44 to provide oxygen to the blood and carbon dioxide removal from the blood. The right ventricle is essentially bypassed by draining the right atrium and pumping into the pulmonary artery thereby allowing the right ventricle to rest.

Utilizing the 72 cm cannula 10 would allow the ECMO circuit to deliver oxygenated blood directly to the lungs and possibly help rest/decompress the Right side (i.e. Tandem-Right cannulation with an oxygenator 44).

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A pumping system for assisting a human patient's heart, comprising:
    a blood pump;
    a drainage cannula adapted for fluid communication with an inlet to the blood pump to provide blood to the blood pump; and
    a blood supply cannula adapted for fluid communication with an outlet of the blood pump to provide blood to the patient's heart arterial system, at least one of the drainage cannula and the blood supply cannula further comprising:
        an elongated body defining a channel extending through the elongated body, the elongated body having a proximal end and a distal end having a distal tip, the distal end defusing at least one of a tip opening communicating with the channel and at least one side hole in proximity to the distal tip and communicating with the channel for outflow of blood at the distal end,
    wherein the drainage cannula has a length to extend from the patient's groin to the patient's right atrium and the blood supply cannula has a length to extend from the patient's groin to the patient's heart arterial system, whereby, when the blood pump operates, the patient's heart and lungs are essentially bypassed by draining the right atrium of blood and pumping blood into the patient's heart arterial system thereby allowing the patient's ventricles to rest and establishing ventricular support.

2. The pumping system as claimed in claim 1, wherein the distal end of the elongated body is curved for natural anatomical placement within the patient's heart.

3. The pumping system as claimed in claim 1, wherein at least a portion of the elongated body has insertion depth markings.

4. The pumping system as claimed in claim 1, wherein the distal tip has radiopaque markers to aid in visualization.

5. The pumping system as claimed in claim 1, further comprising a blood oxygenator between the blood supply cannula and the blood pump outlet to oxygenate the blood received from the patient's heart into the blood pump, the blood pump supplying oxygenated blood to the patient via the blood supply cannula.

6. A method for assisting a human patient's heart, comprising:
    connecting a drainage cannula to an inlet to a blood pump to provide blood to the blood pump, the drainage cannula having a length to extend from the patient's groin to the patient's right atrium;
    connecting a blood supply cannula to an outlet of the blood pump to provide blood to the patient, the blood supply cannula having a length to extend from the patient's groin to the patient's heart arterial system; and
    operating the blood pump such that the patient's ventricles are essentially bypassed by draining the right atrium of blood and pumping blood into the patient's heart arterial system thereby allowing the patient's ventricles to rest and establishing ventricular support.

7. The method as claimed in claim 6, wherein at least one of the drainage cannula and the blood supply cannula further comprises:
    an elongated body defining a channel extending through the elongated body, the elongated body having a proximal end and a distal end having a distal tip, the distal end defining at least one of a tip opening communicating with the channel and at least one side hole in proximity to the distal tip and communicating with the channel for outflow of blood at the distal end.

8. The method as claimed in claim 7, wherein the distal end of the elongated body is curved for natural anatomical placement within the patient's heart.

9. The method as claimed in claim 7, wherein at least a portion of the elongated body has insertion depth markings.

10. The method as claimed in claim 7, wherein the distal tip has radiopaque markers to aid in visualization.

11. The method as claimed in claim 6, further comprising oxygenating the blood received from the patient's heart into the blood pump, the blood pump supplying oxygenated blood to the patient via the blood supply cannula.

12. A pumping system for assisting a human patient's heart, comprising:
    a blood pump;
    a transseptal cannula adapted for fluid communication with an inlet to the blood pump to provide blood to the blood pump; and
    an arterial cannula adapted for fluid communication with an outlet of the blood pump to provide blood to the patient's heart, at least one of the transseptal cannula and the arterial cannula further comprising:
        an elongated body defining a channel extending through the elongated body, the elongated body having a proximal end and a distal end having a distal tip, the distal end defining at least one of a tip opening communicating with the channel and at least one side hole in proximity to the distal tip and communicating with the channel for outflow of blood at the distal end,
    wherein the transseptal cannula is further configured to cross the patient's atrial septum to extend into the patient's left atrium, whereby the patient's left ventricle is essentially bypassed by draining the left atrium when blood is pumped by the blood pump into the patient's heart arterial system via the arterial cannula thereby allowing the patient's left ventricle to rest and establishing left ventricular support.

13. The pumping system as claimed in claim 12, wherein the transseptal cannula has a length to extend from the patient's groin to the patient's heart.

14. The pumping system as claimed in claim 12, wherein the arterial cannula has a length to extend from the patient's groin to the patient's heart.

15. The pumping system as claimed in claim 12, wherein the distal end of the elongated body is curved for natural anatomical placement within the patient's heart.

16. The pumping system as claimed in claim 12, wherein the distal end of the elongated body is curved for natural anatomical placement from the inferior vena cava into the left atrium of the patient's heart.

17. The pumping system as claimed in claim 12, wherein at least a portion of the elongated body has insertion depth markings.

18. The pumping system as claimed in claim 12, wherein the distal tip has radiopaque markers to aid in visualization.

19. The pumping system as claimed in claim 12, further comprising a blood oxygenator between the arterial cannula and the blood pump outlet to oxygenate the blood received from the patient's heart into the blood pump, the blood pump supplying oxygenated blood to the patient via the arterial cannula.

20. A method for assisting a human patient's heart, comprising:
    connecting a transseptal cannula with an inlet to a blood pump to provide blood to the blood pump;

connecting an arterial cannula with an outlet of the blood pump to provide blood to the patient's heart;

crossing the patient's atrial septum using the transseptal cannula whereby the transseptal cannula extends into the patient's left atrium; and operating the blood pump such that the patient's left ventricle is essentially bypassed by draining the left atrium and pumping blood into the patient's heart arterial system via the arterial cannula thereby allowing the patient's left ventricle to rest and establishing left ventricular support, wherein at least one of the transseptal cannula and the arterial cannula further comprises:

an elongated body defining a channel extending through the elongated body, the elongated body having a proximal end and a distal end having a distal tip, the distal end defining at least one of a tip opening communicating with the channel and at least one side hole in proximity to the distal tip and communicating with the channel for outflow of blood at the distal end.

21. The method as claimed in claim 20, wherein the transseptal cannula has a length to extend from the patient's groin to the patient's heart.

22. The method as claimed in claim 20, wherein the arterial cannula has a length to extend from the patient's groin to the patient's heart.

23. The method as claimed in claim 20, wherein the distal end of the elongated body is curved for natural anatomical placement within the patient's heart.

24. The method as claimed in claim 20, wherein the distal end of the elongated body is curved for natural anatomical placement from the inferior vena cava into the left atrium of the patient's heart.

25. The method as claimed in claim 20, wherein at least a portion of the elongated body has insertion depth markings.

26. The method as claimed in claim 20, wherein the distal tip has radiopaque markers to aid in visualization.

27. The method as claimed in claim 20, further comprising oxygenating the blood received from the patient's heart into the blood pump, the blood pump supplying oxygenated blood to the patient via the arterial cannula.

* * * * *

UNITED STATES PATENT AND TRADEMARK OFFICE
CERTIFICATE OF CORRECTION

| | | |
|---|---|---|
| PATENT NO. | : 9,446,183 B2 | Page 1 of 1 |
| APPLICATION NO. | : 14/810701 | |
| DATED | : September 20, 2016 | |
| INVENTOR(S) | : Douglas E. Smith et al. | |

It is certified that error appears in the above-identified patent and that said Letters Patent is hereby corrected as shown below:

Claims

Column 9, Line 16, Claim 1, delete "defusing" and insert -- defining --

Signed and Sealed this
Fifteenth Day of November, 2016

Michelle K. Lee
*Director of the United States Patent and Trademark Office*